United States Patent

Ohashi et al.

Patent Number: 4,480,109
Date of Patent: Oct. 30, 1984

[54] PROCESS FOR PRODUCING THREO-3-(3,4-DIHYDROXYPHENYL)SERINE

[75] Inventors: Naohito Ohashi, Nishinomiya; Shoji Nagata; Kikuo Ishizumi, both of Toyonaka, all of Japan

[73] Assignee: Sumitomo Chemical Company, Limited, Osaka, Japan

[21] Appl. No.: 455,254

[22] Filed: Jan. 3, 1983

[30] Foreign Application Priority Data

Jan. 14, 1982 [JP] Japan .................................. 57-4501
Apr. 20, 1982 [JP] Japan ................................ 57-66491
Apr. 21, 1982 [JP] Japan ................................ 57-67963
Jun. 9, 1982 [JP] Japan .................................. 57-99786

[51] Int. Cl.³ .................... C07C 19/00; C07C 20/00; C07D 317/54; C07D 317/58
[52] U.S. Cl. .................... 549/441; 562/401; 562/446
[58] Field of Search ................ 562/401, 446; 549/441

[56] References Cited

U.S. PATENT DOCUMENTS 3,679,694  7/1972  Rambacher et al. ............. 562/401
3,920,728 11/1975  Hegedus et al. ................. 562/401
4,246,428  1/1981  Ohashi et al. ................... 562/401
4,319,040  3/1982  Ohashi et al. ................... 562/401

Primary Examiner—Natalie Trousof
Assistant Examiner—Vera C. Clarke
Attorney, Agent, or Firm—Stevens, Davis, Miller & Mosher

[57] ABSTRACT

A process for producing an optically active threo-3-(3,4-dihydroxyphenyl)serine represented by the formula

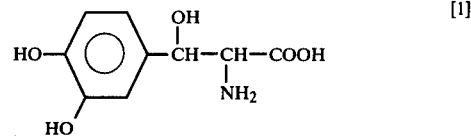

which is useful as a remedy for peripheral orthostatic hypotension or as an antidepressant, which process comprises treating threo-3-(3,4-methylenedioxyphenyl)serine or an N-carbobenzoxy derivative thereof represented by the formula

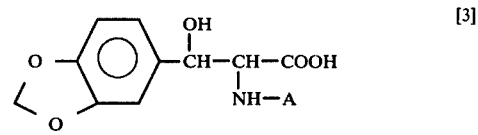

wherein A represents a hydrogen atom or a carbobenzoxy group, with a Lewis acid to form threo-3-(3,4-dihydroxyphenyl)serine or an N-carbobenzoxy derivative thereof represented by the formula

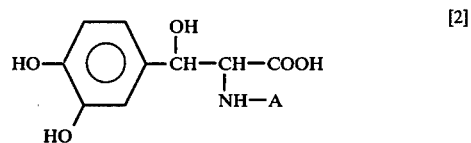

wherein A is as defined above, and, if A is a carbobenzoxy group, catalytically reducing the resulting compound of formula [2]; a racemic or optically active threo-N-carbobenzoxy-3-(3,4-methylenedioxyphenyl)serine represented by the formula

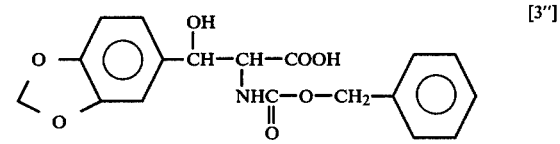

which is a novel compound useful as an intermediate in the above synthesis; and a process for producing said novel compound.

13 Claims, No Drawings

PROCESS FOR PRODUCING THREO-3-(3,4-DIHYDROXYPHENYL)SERINE

This invention relates to a process for producing racemic or optically active threo-3-(3,4-dihydroxyphenyl)serine represented by the formula,

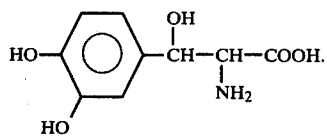 [1]

It relates also to racemic or optically active threo-N-carbobenzoxy*-3-(3,4-methylenedioxyphenyl)serine represented by the formula

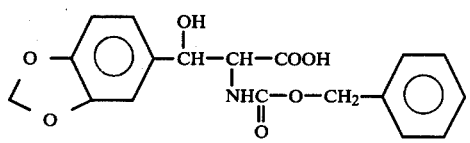 [3″]

which is useful in producing the compound of formula [1], and to process for producing same.
(Note) *or "N-benzyloxycarbonyl".

The optically active threo-3-(3,4-dihydroxyphenyl)serine (hereinafter referred to briefly as DOPS) is known to be a pharmaceutical useful as a remedy for peripheral orthostatic hypotension [Japanese Patent Application "Kokai" (Laid-Open) No. 104,815/81] or as an antidepressant [Japanese Patent Application "Kokai" (Laid-Open) No. 20,747/80].

Known processes for the preparation of optically active DOPS of formula [1] include those disclosed in Japanese Patent Application "Kokai" (Laid-open) Nos. 49,252/75 (Method A), 36,233/79 (Method B), 29,551/81 (Method C), and 32,540/76 (Method D).

In the methods A, B and C, there is employed, as the starting material, a protocatechualdehyde of the formula,

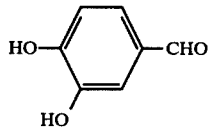

This aldehyde may be obtained for vanilline, veratraldehyde or piperonal wherein its catechol moiety is protected each by a methyl group, two methyl groups or a methylene group. Thus, the procedure of these methods comprises removing the methyl or methylene groups from vanilline, veratraldehyde or piperonal to yield protocatechualdehyde, protecting again the catechol moiety by benzyl groups to form a benzaldehyde derivative of the formula

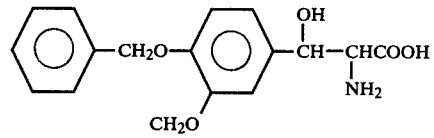

then condensing the resulting derivative with glycine to yield a mixture of threo- and erythro-3-(3,4-dibenzyloxyphenyl)serines of the formula (the formula represents both threo and erythro forms), converting, if necessary, the mixture to appropriate derivative, and separating the mixture into the threo and erythro forms, subjecting each form to optical resolution, and finally removing the protective group to yield an optically active DOPS.

The method D comprises first preparing racemic DOPS from the threo-3-(3,4-dibenzyloxyphenyl)serine obtained as described above, then reacting the resulting racemate with carbobenzoxy chloride (Benzyloxycarbonyl chloride) to yield racemic threo-N-carbobenzoxy-3-(3,4-dihydroxyphenyl)serine, subjecting the resulting protected racemate to optical resolution, and finally removing the protective group to give an optically active DOPS.

As described above, all of the known methods for the preparation of optically active DOPS have in common a disadvantage of adopting a round-about way of synthesis involving replacement of the protective group in catechol moiety of the benzaldehyde derivative used as the starting material. Method D has a further disadvantage in the complicated procedure of preparing racemic DOPS at first, then re-introducing a protective group which is finally removed.

Under the circumstances, the present inventors made an extensive study on the process for producing optically active DOPS without the need of the replacement of a protective group in the catechol moiety. As a result, it was found that optically active DOPS is readily produced by using as the intermediate racemic or optically active threo-N-carbobenzoxy-3-(3,4-methylenedioxyphenyl)serine of formula [3″], which is a novel compound not found in the literature. The present invention has been accomplished on the basis of above discoveries.

More particularly, the present invention is based on the following facts discovered by the present inventors:

1. Racemic threo-3-(3,4-methylenedioxyphenyl)serine acetate can be obtained without any special separation treatment by the condensation of glycine with piperonal.

2. When racemic or optically active threo-N-carbobenozxy-3-(3,4-methylenedioxyphenyl)serine is treated with a Lewis acid, only the methylene portion of the methylenedioxy group can be removed in spite of the presence of carboxyl, carbamate and hydroxyl groups in the same molecule.

3. DL-threo-N-Carbobenzoxy-3-(3,4-methylenedioxyphenyl)serine and DL-threo-N-carbobenzoxy-3-(3,4-dihydroxyphenyl)serine can be optically resolved to yield an optically active (D- or L-) form of the corresponding compounds by using as the resolving agent an optically active amine which is suitable for industrial use.

Accordingly, the invention provides an economical process for the production of optically active DOPS.

On the other hand, although a method is known to form 3-(3,4-methylenedioxyphenyl)serine from glycine and piperonal ["Yakugaku Zasshi" (Journal of the Pharmaceutical Society, Japan), 67, 210 (1947); Can. J. Chem., 42, 1901 (1964)], yet no information has been available on the threo and erythro stereoisomers of said serine compound. The threo stereoisomer has been disclosed and isolated for the first time by the present inventors.

Further, since the threo-3-(3,4-dibenzyloxyphenyl)serine conventionally used as the intermediate in the production of racemic and optically active DOPS is obtained as a mixture of threo and erythro stereoisomers by the reaction between glycine and a benzaldehyde dirivative as stated above, it is necessary to separate the mixture into threo and erythro stereoisomers [G. Am. Chem. Soc., 76, 1322 (1954); Japanese Patent Application "Kokai" (Laid-open) Nos. 49,252/75 and 19,931/79]. As contrasted, according to this invention the threo-3-(3,4-methylenedioxyphenyl)serine is readily obtained without the need of special separation procedure.

The racemic threo-N-carbobenzoxy-3-(3,4-methylenedioxyphenyl)serine is a novel compound obtained by the reaction of racemic threo-3-(3,4-methylenedioxyphenyl)serine with carbobenzoxy chloride. An optically active threo-3-(3,4-methylenedioxyphenyl)serine is obtained by reacting said racemic N-carbobenzoxy derivative with one of the optically active amines including ephedrine, quinidine, quinine and 2-amino-1,1-diphenylpropanol to yield a mixture of amine salts of D- and L-threo-N-carbobenzoxy-3-(3,4-methylenedioxyphenyl)serine, separating the mixture by taking advantage of the solubility difference into the amine salt of D-threo-N-carbobenzoxy-3-(3,4-methylenedioxyphenyl)serine and the amine salt of L-threo-N-carbobenzoxy-3-(3,4-methylenedioxyphenyl)serine, and finally reacting each amine salt with an acid.

There is no known method for converting a racemic or optically active threo-N-carbobenzoxy-3-(3,4-methylenedioxyphenyl)serine into corresponding threo-N-carbobenzoxy-3-(3,4-dihydroxyphenyl)serine. Various methods are known for the removal of methylene group from the compound having a methylenedioxy group to form a catechol group. However, as for the compound having amino and carboxyl groups in addition to the methylenedioxy group, there is found a report about the case where 3-(3,4-methylenedioxyphenyl)alanine or an N-acetyl derivative thereof is treated with hydroiodic acid and acetic anhydride in the presence of red phosphorus to obtain 3-(3,4-dihydroxyphenyl)alanine [Chem. Pharm. Bull., 10, 693 (1962)]. No report was found in the case of compound having hydroxyl, carbamate, carboxyl, and methylenedioxy groups all together. The present inventors, therefore, conducted an extensive study on the conversion of a racemic or optically active threo-N-carbobenzoxy-3-(3,4-methylenedioxyphenyl)serine having hydroxyl, carbamate, and carboxyl groups in addition to the methylenedioxy group into corresponding racemic or optically active threo-N-carbobenzoxy-3-(3,4-dihydroxyphenyl)serine. It was found, as a result, that it is possible to achieve the conversion by the treatment with a Lewis acid under mild conditions. The addition of a mercaptan along with the Lewis acid is favorable to the reaction.

The method for the formation of an optically active threo-N-carbobenzoxy-3-(3,4-dihydroxyphenyl)serine from racemic threo-N-carbobenzoxy-3-(3,4-dihydroxyphenyl)serine by the optical resolution technique is known [Japanese Patent Application "Kokai" (Laid-open) No. 32,540/76]. In the known method, an expensive resolving agent, quinine is used. The present inventors investigated the resolution with a resolving agent available at low cost or one which is easily prepared. As a result, it was found that the optical resolution is possible by using as the resolving agent cinchonidine, brucine or ephedrine, all of which are available at a lower cost than quinine, or 2-amino-1,1-diphenylpropanol which is easily prepared [Japanese Patent Application "Kokai" (Laid-Open) No. 141666/79]. It is thus possible to obtain an optically active threo-N-carbobenzoxy-3-(3,4-dihydroxyphenyl)serine by reacting racemic threo-N-carbobenzoxy-3-(3,4-dihydroxyphenyl)serine with an optically active amine selected from cinchonidine, brucine, ephedrine, and 2-amino-1,1-diphenylpropanol to yield a mixture of amine salts of D- and L-threo-N-carbobenzoxy-3-(3,4-dihydroxyphenyl)serine, separating the mixture by taking advantage of the solubility difference into the amine salt of D-threo-N-carbobenzoxy-3-(3,4-dihydroxyphenyl)serine and the amine salt of L-threo-N-carbobenzoxy-3-(3,4-dihydroxyphenyl)serine, and finally reacting each amine salt with an acid.

The conversion of an optically active threo-N-carbobenzoxy-3-(3,4-dihydroxyphenyl)serine into optically active DOPS is achieved under the reaction conditions commonly employed in removing the carbobenzoxy group in the reactions of amino acids or peptides.

The process of the present invention is schematically represented in the following Figure.

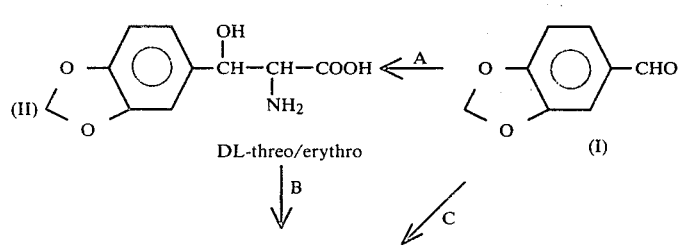

-continued

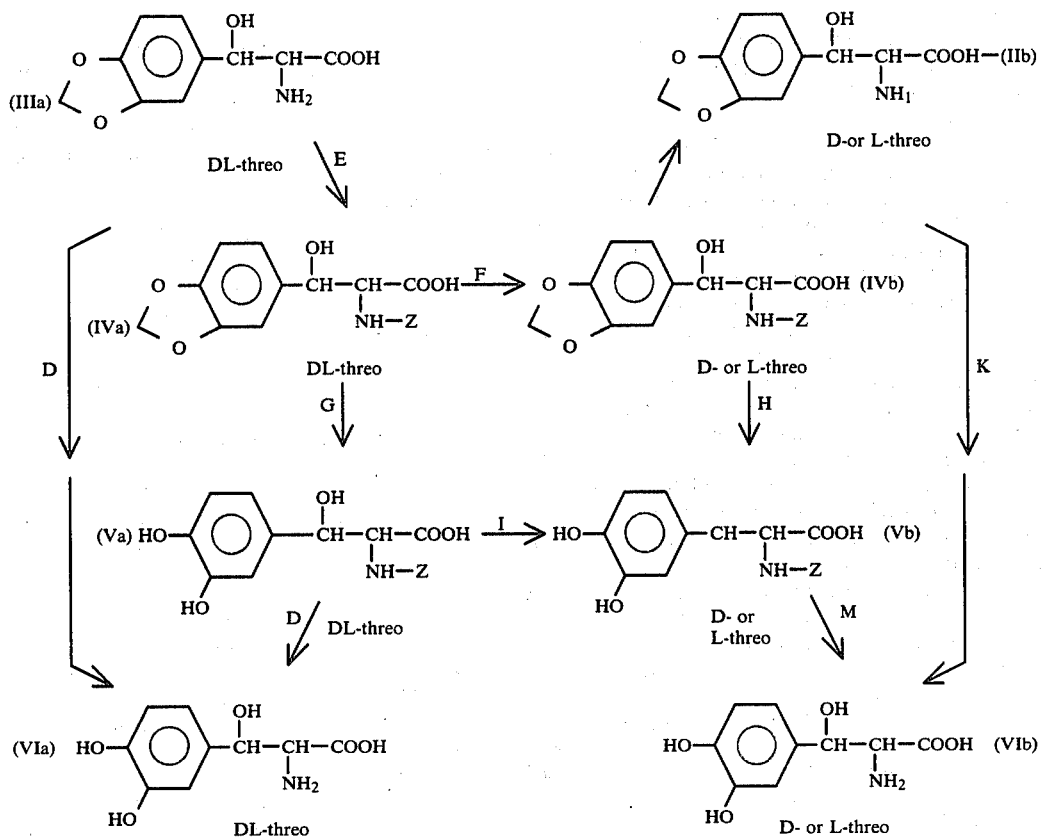

(Note)
Z: Carbobenzoxy group

Each step of the process is described below in detail.

Step A (Compound I→II):

Compound II, threo/erythro-3-(3,4-methylenedioxyphenyl)serine, is obtained in the form of crystalline acetate by the reaction of 1 mole of glycine, 2 moles of piperonal (I) and 2 moles of a base such as sodium hydroxide or potassium hydroxide in a solvent such as methanol, ethanol or the like, at a temperature of 50°–70° C. for 0.5–2 hr and subsequent treatment of the reaction product with aqueous acetic acid.

Step B (Compound II→IIIa):

In this step, crystalline threo-3-(3,4-methylenedioxyphenyl)serine (IIIa) is obtained from the acetate of threo/erythro-3-(3,4-methylenedioxyphenyl)serine, a mixture of threo and erythro forms, by recrystallizing from water or by suspending the acetate in water and collecting the suspended matter by filtration, whereby the separation of threo form from erythro form takes place. In this step, there is obtained free amino acid from the acetate with the elimination of acetic acid moiety. Although no special restriction is posed on the ratio of threo form to erythro form, it is prefered that the mixture contains excess threo form. The recrystallization is performed in the usual manner. When the separation is to be effected by suspending the acetate in water followed by filtration, the threo form (IIIa) is obtained by adding water in an amount of about 5 to 15 times the quantity of acetate, stirring the resulting suspension at 20° to 60° C., then cooling to 0° to 30° C., and filtering. The stirring in water can be performed at room temperature or thereabout.

Step C (Compound I→IIIa)

The acetate of racemic threo-3-(3,4-methylenedioxyphenyl)serine (IIIa) is also obtained directly by the condensation of glycine and piperonal in the presence of a base and subsequent addition of acetic acid to the reaction mixture. Piperonal and the base are used in an amount of preferably 2 to 3 moles and 1.5 to 2.5 moles, respectively, per 1 mole of glycine. Suitable bases are inorganic ones such as sodium hydroxide, potassium hydroxide, sodium carbonate, potassium carbonate, and the like. The reaction media are alcoholic solvents such as methanol, ethanol, and isopropyl alcohol, ether-type solvents such as tetrahydrofuran and dioxane, and mixtures of these solvents with water. The condensation temperature and the reaction time are in the range of from −10° to 40° C. and 5–20 hr, respectively, in order to minimize the accompanying racemic erythro-3-(3,4-methylenedioxyphenyl)serine. After completion of the condensation, the intermediate products of the reaction are decomposed by the addition of water and acetic aicd. To the reaction mixture is added an organic solvent such as toluene, benzene, ethyl acetate, and diethyl ether in order to transfer the piperonal to the organic layer and to collect precipitated acetate of racemic threo-3-(3,4-methylenedioxyphenyl)serine. The amount of water to be added is twice or more times, preferably 3 to 20 times the weight of glycine and the amount of acetic acid is three or more times, preferably 5 to 30 times the weight of glycine.

In the above procedure, the threo form precipitates in the form of acetate, whereas the erythro form remains as dissolved in the medium. Although racemic 3-(3,4-methylenedioxyphenyl)serine of unknown steric configuration (threo-erythro isomerism) is already known [Yakugaku Zasshi, 67, 218 (1947); Can. J. Chem., 42, 1901 (1964)], the threo form has been isolated and identified for the first time by the present inventors.

Step D (Compound IIIa→VIa):

In this step, threo-3-(3,4-methylenedioxyphenyl)serine is treated with a Lewis acid to give DOPS (VIa). Examples of preferable Lewis acids are aluminum chloride, aluminum bromide, ferric chloride, stannic chloride, boron trichloride, and boron tribromide. It is also possible to use a complex of a Lewis acid and dimethyl sulfide. The amount to be used of Lewis acid is 1 to 20, preferably 2 to 10, moles per 1 mole of threo-3-(3,4-methylenedioxyphenyl)serine (IIIa). In some cases, favorable results are obtained by adding to the reactant mixture, in addition to the Lewis acid, a mercaptan such as methylmercaptan, ethylmercaptan, butylmercaptan, octylmercaptan, dodecanylmercaptan, octadecanylmercaptan or thiophenol in an amount of 1 to 4 moles per 1 mole of the Lewis acid. Any solvent which does not interfere with progress of the reaction may be used as the reaction medium. Preferable solvents include halogenated hydrocarbon-type solvents such as dichloromethane, chloroform, dichloroethane, and chlorobenzene; aromatic hydrocarbons such as toluene and benzene; esters such as ethyl acetate and butyl acetate; nitrohydrocarbons such as nitromethane, nitroethane, and nitrobenzene; and ketones such as acetone and methyl ethyl ketone. If necessary, DOPS which is produced can be recrystallized from water.

The above procedure is applicable to both the racemate and the optically active isomers.

Step E (Comound IIIa→IVa):

Racemic threo-N-carbobenzoxy-3-(3,4-methylenedioxyphenyl)serine (IVa) is obtained by so-called Schotten-Baumann reaction between racemic threo-3-(3,4-methylenedioxyphenyl)serine (IIIa) and carbobenzoxy chloride. This reaction is carried out by adding the latter to an alkaline aqueous solution (pH 7 or above) of the former. The amount by mole used of the latter is 1 to 2 times the amount of the former. The reaction is allowed to proceed at a reaction temperature of 0° to 30° C. for several minutes to 20 hours. It is preferable to maintain pH at 7 to 10 during the reaction by the dropwise addition of an aqueous alkali solution to keep the pH at the predetermined level or by the prior addition of sodium hydrogencarbonate, borax, or the like to the reactor so as to keep the aqueous solution at pH 7–10. Alkalis for use in the alkaline aqueous solution include sodium hydrogencarbonate, sodium carbonate, potassium carbonate, sodium hydroxide, and potassium hydroxide. The reaction proceeds sufficiently in an aqueous solution. If required, there may be added aromatic hydrocarbons such as toluene and benzene; aliphatic hydrocarbons such as hexane and heptane; ethers such as diethyl ether, tetrahydrofuran, and dioxane; ketones such as acetone and methyl ethyl ketone; alkyl halide-type solvents such as chloroform, dichloromethane, and dichloroethane; esters such as ethyl acetate and butyl acetate; and mixtures of these solvents.

Step F (Compound IVa→IVb):

An optically active threo-N-carbobenzoxy-3-(3,4-methylenedioxyphenyl)serine (IVb) is obtained by reacting, in a suitable solvent, racemic threo-N-carbobenzoxy-3-(3,4-methylenedioxyphenyl)serine (IVa) with an optically active amine selected from ephedrine, quinidine, quinine, and 2-amino-1,1-diphenylpropanol to yield the salts of D- and L-threo-N-carbobenzoxy-3-(3,4-methylenedioxyphenyl)serine with the optically active amine, separating the salts into the salt of D-threo-N-carbobenzoxy-3-(3,4-methylenedioxyphenyl)serine with the optically active amine and the salt of L-threo-N-carbobenzoxy-3-(3,4-methylenedioxyphenyl)serine with the optically active amine by taking advantage of the solubility difference, and decomposing each salt with an acid.

The formation and fractionation of the amine salt are performed at 0° to 80° C., or by heating to a temperature near the boiling point of the solvent and cooling to 0° C. to 30° C. The formation of the amine salt is complete within several minutes but the reaction time can be extended to several hours wihtout causing any disturbance. The molar ratio of the optically active amine to the racemic threo-N-carbobenzoxy-3-(3,4-methylenedioxyphenyl)serine is from 0.5 to 1. Examples of solvents suitable for the formation and fractionation of the amine salts, are alcohols such as methanol, ethanol, and isopropyl alcohol; ethers such as tetrahydrofuran and dioxane; acetonitrile, water, and mixtures of these solvents.

The optically active threo-N-carbobenzoxy-3-(3,4-methylenedioxyphenyl)serine is obtained by adding an aqueous acidic solution to the salt of optically active threo-N-carbobenzoxy-3-(3,4-methylenedioxyphenyl)serine with the optically active amine to decompose the salt, and extracting with an organic solvent. The acids suitable for use in the aqueous acidic solution are mineral acids such as hydrochloric acid, sulfuric acid, and phosphoric acid. The amount by mole to be used of the acid is 1 to 10 times the amount of amine salt. The organic solvents suitable for the extraction include ethyl acetate, chloroform, dichloroethane, dichloromethane, and diethyl ether.

The racemic and optically active threo-N-carbobenzoxy-3-(3,4-methylenedioxyphenyl)serine (IVa and IVb), which are novel compounds not found in the literature, have an antimicrobial activity by themselves and are useful not only as the intermediates in synthesizing DOPS, but also as pharmaceuticals by themselves.

Step G (Compound IVa→Va) and
Step H (Compound IVb→Vb):

When racemic or optically active threo-N-carbobenzoxy-3-(3,4-methylenedioxyphenyl)serine (IVa and IVb) is treated with a Lewis acid in a suitable solvent, there is obtained corresponding racemic or optically active threo-N-carbobenzoxy-3-(3,4-dihydroxyphenyl)serine (Va and Vb). Examples of suitable Lewis acids are aluminum chloride, aluminum bromide, ferric chloride, stannic chloride, boron trichloride, and boron tribromide. A complex of a Lewis acid and dimethyl sulfide may also be used as a Lewis acid. The amount to be used of a Lewis acid is 1 to 20, preferably 2 to 10, moles per 1 mole of threo-N-carbobenzoxy-3-(3,4-methylenedioxyphenyl)serine. To obtain more desirable results, there may be added to the reactant mixture, in addition to a Lewis acid, a mercaptan of 1 to 20 carbon atoms such as methylmercaptan, ethylmercaptan, butylmercaptan, octylmercaptan, dodecanylmercaptan, octadecanylmercaptan and thiophenol, in an amount of 1 to 5 moles per 1 mole of Lewis acid. Although any of the solvents which do not interfere with the progress of the reaction may be used, preferable solvents are halogenated hydrocarbon-type solvents such as dichloromethane, chloroform, dichloroethane, and chlorobenzene; aromatic hydrocarbons such as toluene and benzene; esters such as ethyl acetate and butyl acetate; nitrohydrocarbons such as nitromethane, nitroethane, and nitrobenzene; ketones such as acetone and methyl ethyl ketone; pyridine, and mixtures of these solvents. The reaction is carried out at a temperature in the range of from $-40°$ to $80°$ C., preferably from $-10°$ to $30°$ C. The reaction is complete within the range of from 10 minutes to 4 hours. A more extended reaction time has no adverse effect.

Step I (Compound Va→Vb):

An optically active threo-N-carbobenzoxy-3-(3,4-dihydroxyphenyl)serine (Vb) is obtained by reacting racemic threo-N-carbobenzoxy-3-(3,4-dihydroxyphenyl)serine (Va) with an optically active amine selected from cinchonidine, brucine, ephedrine, and 2-amino-1,1-diphenylpropanol to yield the amine salts of D- and L-threo-N-carbobenzoxy-3-(3,4-dihydroxyphenyl)serine, separating the salts into the amine salt of D-threo-N-carbobenzoxy-3-(3,4-dihydroxyphenyl)serine and the amine salt of L-threo-N-carbobenzoxy-3-(3,4-dihydroxyphenyl)serine by taking advantage of the solubility difference, and reacting each amine salt with an acid. The optical resolution and the decomposition of salt described above can be carried out under the same conditions of molar ratio, solvent, temperature, and time as used in Step F, except for the optically active amine.

Steps J and K (Compound IVb→IIIb→VIb):

An optically active threo-3-(3,4-methylenedioxyphenyl)serine (IIIb) is obtained by the catalytic reduction of an optically active threo-N-carbobenzoxy-3-(3,4-methylenedioxyphenyl)serine (IVb). A catalyst such as palladium, platinum, or nickel, either unsupported or supported on a carrier such as barium carbonate or activated carbon is used in a weight ratio of 0.01–0.1 against unit weight of optically active threo-N-carbobenzoxy-3-(3,4-methylenedioxyphenyl)serine (IVb). Solvents suitable for use in the above reaction include alcohols such as methanol and ethanol; aromatic hydrocarbons such as benzene and toluene; esters such as ethyl acetate; ketones such as acetone and methyl ethyl ketone; water, and mixtures of any of these solvents. The reaction proceeds at room temperature or at a temperature higher or lower than room temperature with heating or cooling. The hydrogen pressure can be either atmospheric or superatmospheric. It is possible to add an acid such as hydrochloric acid or sulfuric acid to the reaction system to promote the reaction.

In the next step, the optically active threo-3-(3,4-methylenedioxyphenyl)serine (IIIb) is treated with a Lewis acid as in the aforementioned step D, G, or H to yield an optically active threo-3-(3,4-dihydroxyphenyl)serine (VIb). Examples of suitable Lewis acids are aluminum chloride, aluminum bromide, ferric chloride, stannic chloride, boron trichloride, and boron tribromide. A complex of a Lewis acid and dimethyl sulfide can be used as a Lewis acid. The amount by mole to be used of a Lewis acid is 1 to 20, preferably 2 to 10, moles per 1 mole of threo-3-(3,4-methylenedioxyphenyl)serine (IIIb). In some cases, favorable results are obtained by adding to the reactant mixture, in addition to the Lewis acid, a mercaptan such as methylmercaptan, ethylmercaptan, butylmercaptan, octylmercaptan, dodecanylmercaptan, octadecanylmercaptan or thiophenol in an amount of 1 to 4 moles per 1 mole of the Lewis acid. Although any of the solvents which do not interfere with the progress of reaction may be used as the reaction medium, preferable solvents are halogenated hydrocarbon-type solvents such as dichloromethane, chloroform, dichloroethane, and chlorobenzene; aromatic hydrocarbons such as toluene and benzene; esters such as ethyl acetate and butyl acetate; nitrohydrocarbons such as nitromethane, nitroethane, and nitrobenzene; and ketones such as acetone and methyl ethyl ketone.

Step L (Compound Va→VIa):

Racemic threo-3-(3,4-dihydroxyphenyl)serine (VIa) is prepared from racemic threo-N-carbobenzoxy-3-(3,4-dihydroxyphenyl)serine (Va) by eliminating the carbobenzoxy group under normal conditions such as those described above in Step J or below in Stem M.

Step M (Compound Vb→VIb):

An optically active threo-3-(3,4-dihydroxyphenyl)serine (VIb) is prepared by the catalytic reduction of optically active threo-N-carbobenzoxy-3-(3,4-dihydroxyphenyl)serine (Vb). A catalyst such as palladium, platinum, or nickel, either unsupported or supported on a carrier such as barium carbonate or activated carbon is used in a weight ratio of 0.01–0.1 against unit weight of optically active threo-N-carbobenzoxy-3-(3,4-dihydroxyphenyl)serine (Vb). Solvents suitable for use in the above reaction include alcohols such as methanol and ethanol; aromatic hydrocarbons such as benzene and toluene; esters such as ethyl acetate; ketones such as acetone and methyl ethyl ketone; water, and mixtures of any of these solvents. The reaction proceeds at room temperature or at a temperature higher or lower than room temperature with heating or cooling. The hydrogen pressure can be either atmospheric or superatmospheric. It is possible to add an acid such as hydrochloric acid or sulfuric acid to the reaction system to promote the reaction.

The invention is illustrated below in detail with reference to Examples, but the invention is not limited thereto.

EXAMPLE 1

Synthesis of racemic erythro- and threo-3-(3,4-methylenedioxyphenyl)serine.

To a solution of 61.1 g of potassium hydroxide and 33.05 g of glycine in 1055 ml of methanol, was added 145 g of piperonal at 30° C. or below. The mixture was then stirred at 62° to 65° C. for 30 minutes. The reaction mixture was concentrated and the residue was dissolved in 135 ml of methanol. To the solution was added 808 g of acetic acid at 30° C. or below. The mixture was then stirred at 40° to 45° C. for 30 minutes. After addition of 135 g of water and 1,250 ml of toluene, the mixture was stirred at 40° to 45° C. for 2 hours, then at 0° to 5° C. for 1 hour. The precipitated crystals were collected by filtration to obtain 86.98 g (69.3% yield) of racemic erythro/threo-3-(3,4-methylenedioxyphenyl)serine acetate.

Mp. 162° C. (decomp.).

IR (Nujol) $\nu(cm^{-1})$: 3550–2200 (broad), 3490, 1720, 1670, 1580, 1490, 1400, 1290, 1050, 940.

HPLC analysis: erythro/threo=16/84.

Conditions for HPLC:

Column: Lichromosorb BP-18, 10$\mu$, 4 cm×30 cm.

Moving phase solvent: 0.005 M PIC B-7 acetonitrile (9:1).

Flow rate: 1.0 ml/min.

Detection: UV (254 nm)

Elution time: erythro isomer: 7.5 min. threo isomer: 8.5 min.

The filtrate was left standing at room temperature for 15 hours and the precipitated crystals were collected by filtration to obtain 2.36 g (4.8% yield) of racemic erythro-3-(3,4-methylenedioxyphenyl)serine acetate.

Mp. 138.5° C. (decomp.).

IR (Nujol) ν(cm⁻¹): 3490, 3400–2200 (broad), 1695, 1590, 1510, 1400, 1240, 1040, 935.

NMR (DMSO-$d_6$) δ: 1.88 (3H, s), 3.44 (1H, d, J-7 Hz), 4.89 (1H, d, J-7 Hz), 5.40 (2H, s), 6.74–7.00 (3H, m).

EXAMPLE 2

(1) A mixture of 1,105 g of water and 85 g of threo/erythro-3-(3,4-methylenedioxyphenyl)serine acetate was heated with stirring under reflux to form a solution. The solution was cooled and stirred at 0° to 5° C. for 1 hour. The precipitated crystals were collected by filtration and dried to yield 48.37 g (72.1% yield) of threo-3-(3,4-methylenedioxyphenyl)serine.

Mp. 193° C. (decomp.).

IR (Nujol) ν(cm⁻¹): 3600–2100 (broad), 3550, 3460, 1680, 1510, 1440, 1400, 1370, 1250, 1040, 930.

NMR (DMSO-$d_6$) δ: 3.34 (1H, d, J=4 Hz), 4.97 (1H, d, J=4 Hz), 5.68 (2H, s).

HPLC analysis: erythro/threo=0/100

(2) A mixture of 20 g of water and 1 g of threo/erythro-3-(3,4-methylenedioxyphenyl)serine acetate was stirred at room temperature for 30 minutes. The precipitated crystals were collected by filtration and dried to give 0.45 g (57.0% yield) of threo-3-(3,4-methylenedioxyphenyl)serine.

Mp. 188° C. (decomp.).

HPLC analysis under the conditions given above: threo:erythro=98.7:1.3.

EXAMPLE 3

Synthesis of racemic threo-3-(3,4-methylenedioxyphenyl)serine.

A solution of 45.4 g of glycine, 203.2 g of piperonal and 87.7 g of potassium hydroxide in 338 g of methanol was stirred at room temperature for 5 hours. After addition of 637 g of acetic acid, the mixture was stirred at 35° to 45° C. for 30 minutes. The reaction mixture was diluted with 181 g of water and stirred at room temperature for 4 hours. Then, 157 g of toluene was added to the mixture and stirring was continued for 2 hours. The precipitated crystals were collected by filtration and washed with toluene to yield 120.6 g of racemic threo-3-(3,4-methylenedioxyphenyl)serine acetate melting at 161° C. (decomp.).

IR (Nujol) ν(cm⁻¹): 3460–2200 (broad), 1705, 1665, 1610, 1490, 1400, 1285, 1240, 1040, 930, 840.

NMR (DMSO-$d_6$) δ: 1.9 (3H, s), 3.47 (1H, d, J=4 Hz), 4.99 (1H, d, J=4 Hz), 5.96 (2H, s), 6.76–6.97 (3H, m).

The filtrate and washings were combined, diluted with 500 g of water, and allowed to separate into two layers. The toluene layer was washed with a 5% aqueous sodium hydroxide solution, then with water, and concentrated under reduced pressure to recover 87.2 g of piperonal.

EXAMPLE 4

Synthesis of racemic threo-3-(3,4-dihydroxyphenyl)serine from racemic threo-3-(3,4-methylenedioxyphenyl)serine.

To a mixture of 1.5 g of racemic threo-3-(3,4-methylenedioxyphenyl)serine, 1.5 ml of dichloromethane, and 1.5 ml of ethylmercaptan, while being cooled in ice and stirred, was added 7.11 g of anhydrous aluminum bromide. The mixture was stirred with colling in ice for 3 hours, then at room temperature for 15 hours. After addition of 60 ml of 10% hydrochloric acid, the mixture was allowed to separate into two layers. The aqueous layer was adjusted to pH about 5 with sodium hydroxide. The precipitated crystals were collected by filtration and recrystallized from 30 ml of water containing 15 mg of L-ascorbic acid to yield 1.1 g of racemic threo-3-(3,4-dihydroxyphenyl)serine melting at 226° C. (decomp.).

EXAMPLE 5

Synthesis of racemic threo-N-carbobenzoxy-3-(3,4-methylenedioxyphenyl)serine.

(1) Into a solution of 30.4 g of sodium hydroxide in 1,217.8 g of water, was dissolved 108.6 g of racemic threo-3-(3,4-methylenedioxyphnyl) serine acetate. To the solution cooled in ice, was added dropwise 102 g of a 70% solution of carbobenzoxy chloride in toluene, accompanied by simultaneous dropwise addition of a 30% aqueous sodium hydroxide solution to adjust pH to about 8.5–9.5. After completion of the addition of carbobenzoxy chloride, the mixture was allowed to react for 4 hours, while the cooling in ice and the pH adjustment being continued. The reaction mixture was then adjusted to pH about 1 with 120 g of concentrated hydrochloric acid, diluted with 350 g of toluene, and stirred at 40°–45° C. for 1 hour, then at 5°–10° C. for two hours. The precipitated crystals were collected by filtration, washed with water, then with toluene to yield 347.4 g of racemic threo-N-carbobenzoxy-3-(3,4-methylenedioxyphenyl)serine.

Mp. 136°–138° C.

IR (Nujol) ν(cm⁻¹): 3500, 3250, 1750, 1655, 1505, 1340, 1255, 1220, 1160.

(2) To 160 ml of an aqueous solution containing 4.0 g of sodium hydroxide, while being cooled at 5° C. or below, was added 11.3 g of racemic threo-3-(3,4-methylenedioxyphenyl)serine. After complete dissolution, to the solution, while being cooled at 5° C. or below, was added dropwise 9.4 g of carbobenzoxy chloride, accompanied by simultaneous dropwise addition of a 30% aqueous sodium hydroxide solution to adjust pH to 8.5–9.5. After 2 hours, the reaction mixture was adjusted to pH about 2 with concentrated hydrochloric acid and extracted with ethyl acetate. The organic layer was washed with saturated aqueous sodium chloride solution, dried over magnesium sulfate, and concentrated under reduced pressure. The residue was crystallized by toluene and the crystals were collected by filtration to give 17.3 g of racemic threo-N-carbobenzoxy-3-(3,4-methylenedioxyphenyl)serine.

Mp.: 136°–138° C.

IR (Nujol) ν(cm⁻¹): 3500, 3250, 1750, 1655, 1505, 1340, 1255, 1220, 1160.

EXAMPLE 6

Synthesis of optically active threo-N-carbobenzoxy-3-(3,4-methylenedioxyphenyl)serine.

(1) To a solution of 10.0 g of racemic threo-N-carbobenzoxy-3-(3,4-methylenedioxyphenyl)serine in 100 ml of acetonitrile, was added 9.02 g of quinidine to form a uniform solution. The solution was cooled in iced water for 5 hours and the precipitated crystals were collected by filtration to yield 9.0 g of L-threo-N-carbobenzoxy-3-(3,4-methylenedioxyphenyl)serine quinidine salt.

Mp.: 161°–163° C.

$[\alpha]_D^{20}$ +119.5° (c=1.0, methanol).

A 2.0 g portion of the above salt was mixed with 5 ml of 3-% hydrochloric acid and extracted with ethyl acetate to obtain 0.98 g of an amorphous powder of L-threo-N-carbobenzoxy-3-(3,4-methylenedioxyphenyl)serine.

IR (Nujol) $\nu(cm^{-1})$: 3500–3250 (broad), 1740–1670 (broad), 1890, 1440, 1040, 930.

$[\alpha]_D^{20} -24.5°$ (c=1.0, methanol).

Another portion, weighing 6.0 g, of the above salt was recrystallized twice from methanol to yield 4.4 g of purified salt; mp. 162°–163.5° C.; $[\alpha]_D^{20} +122.6°$ (c=1.0, methanol). A 4.0 g portion of the purified salt was mixed with 3-% hydrochloric acid, and extracted with ethyl acetate to obtain 1.8 g of an amorphous powder of L-threo-N-carbobenzoxy-3-(3,4-methylenedioxyphenyl)serine.

$[\alpha]_D^{20} -28.1°$ (c=1.0, methanol).

(2) To 10.0 g of racemic threo-N-carbobenzoxy-3-(3,4-methylenedioxyphenyl)serine, were added 100 ml of isopropyl alcohol and 9.02 g of quinidine to form a uniform solution. The solution was left standing overnight at room temperature and the precipitated crystals were collected by filtration to yield 8.3 g of L-threo-N-carbobenzoxy-3-(3,4-methylenedioxyphenyl)serine quinidine salt.

Mp.: 161°–163° C.

$[\alpha]_D^{20} +119.8°$ (c=1.0, methanol).

A 4.0 g portion of the salt was mixed with 3-% hydrochloric acid and extracted with ethyl acetate to obtain 1.9 g of an amorphous powder of L-threo-N-carbobenzoxy-3-(3,4-methylenedioxyphenyl)serine.

$[\alpha]_D^{20} -25.3°$ (c=1.0, methanol).

(3) To a solution of 5.0 g of racemic threo-N-carbobenzoxy-3-(3,4-methylenedioxyphenyl)serine in 50 ml of acetonitrile, was added 4.5 g of quinine to form a uniform solution. The solution was left standing overnight at room temperature and the precipitated crystals were collected by filtration to yield 5.1 g of D-threo-N-carbobenzoxy-3-(3,4-methylenedioxyphenyl)serine quinine salt.

Mp.: 116°–118° C.

$[\alpha]_D^{20} -97.3°$ (c=1.0, methanol).

A 4.0 g portion of the salt was mixed with 3-% hydrochloric acid, extracted with ethyl acetate to obtain 2.0 g of an amorphous powder of D-threo-N-carbobenzoxy-3-(3,4-methylenedioxyphenyl)serine.

$[\alpha]_D^{20} +18.0°$ (c=1.0, methanol).

(4) Into 100 ml of ethanol, were dissolved 10.0 g of racemic threo-N-carbobenzoxy-3-(3,4-methylenedioxyphenyl)serine and 6.3 g of R-2-amino-1,1-diphenylpropanol. The solution was cooled in ice for 4 hours. The precipitated crystals were collected to yield 7.8 g of R-2-amino-1,1-diphenylpropanol salt of L-threo-N-carbobenzoxy-3-(3,4-methylenedioxyphenyl)serine.

Mp.: 170.5° C. (decomp.).

$[\alpha]_D^{20} -23.1°$ (c=1.0, methanol).

A 4.0 g portion of the salt was mixed with 100 ml of 3-% hydrochloric acid and extracted with ethyl acetate to yield 2.3 g of L-threo-N-carbobenzoxy-3-(3,4-methylenedioxyphenyl)serine in the form of amorphous powder.

$[\alpha]_D^{20} -26.8°$ (c=1.0, methanol).

(5) To 10.0 g of racemic threo-N-carbobenzoxy-3-(3,4-methylenedioxyphenyl)serine, were added 4.6 g of l-ephedrine and 200 ml of ethanol. The resulting solution was cooled in ice for 6 hours. The precipitated salt was collected by filtration and recrystallized twice from ethanol to yield 5.3 g of l-ephedrine salt of D-threo-N-carbobenzoxy-3-(3,4-methylenedioxyphenyl)serine.

Mp.: 177°–178° C.

$[\alpha]_D^{20} -22.2°$ (c=1.0, methanol).

A portion, 2.0 g in weight, of the salt was mixed with 3-% hydrochloric acid and extracted with ethyl acetate to obtain 1.3 g of an amorphous powder of D-threo-N-carbobenzoxy-3-(3,4-methylenedioxyphenyl)serine.

$[\alpha]_D^{20} +28.0$ (c=1.0, methanol).

EXAMPLE 7

Sunthesis of racemic threo-N-carbobenzoxy-3-(3,4-dihydroxyphenyl)serine.

(1) To 18 g of racemic threo-N-carbobenzoxy-3-(3,4-methylenedioxyphenyl)serine, were added 500 ml of dichloromethane and 30 ml of ethylmercaptan. The mixture was stirred while being cooled at 5° C. The resulting solution was mixed with 27.6 g of aluminum chloride and allowed to react at 5° C. or below for 4 hours. The reaction mixture was mixed with 250 ml of 10-% hydrochloric acid and allowed to separate into 2 layers. The dichloromethane layer was removed and the aqueous aqueous layer was extracted with ethyl acetate. The ethyl acetate layer was washed with saturated aqueous sodium chloride solution, dried over anhydrous magnesium sulfate, and concentrated under reduced pressure, leaving behind 14.7 g of a residue. The residue was purified by silica gel chormatography (elution solvent: acetonitrile/benzene/acetic acid=4.5/4.5/1) to yield 12.8 g of an amorphous powder of racemic threo-N-carbobenzoxy-3-(3,4-dihydroxyphenyl)serine. The amorphous powder was crystallized in ethyl acetate to give 10.6 g of crystals.

Mp.: 145°–146° C. (decomp.).

IR (Nujol) $\nu(cm^{-1})$: 3520, 3490, 3330, 3270, 1720, 1700, 1610, 1535, 1290, 1175, 1080, 1055, 990.

(2) Using 18 g of racemic threo-N-carbobenzoxy-3-(3,4-methylenedioxyphenyl)serine, 500 ml of dichloromethane, 118 g of n-octadecylmercaptan, and 27.6 g of aluminum chloride, the reaction and the after-treatment were carried out as in (1) above. There was obtained 19.5 g of the residue which was crystallized from ethyl acetate to give 11.7 g of racemic threo-N-carbobenzoxy-3-(3,4-dihydroxyphenyl)serine; Mp. 145°–146° C. (decomp.).

(3) The reaction, after-treatment and crystallization were carried out as in (2) above, using 500 ml toluene in place of 500 ml of the dichloromethane used in (2) above. There were obtained 9.0 g of racemic threo-N-carbobenzoxy-3-(3,4-dihydroxyphenyl)serine: Mp. 144°–146° C. (decomp.).

EXAMPLE 8

Synthesis of optically active threo-N-carbobenzoxy-3-(3,4-dihydroxyphenyl)serine from optically active threo-N-carbobenzoxy-3-(3,4-methylenedioxyphenyl)serine.

(1) To 8.0 g of L-threo-N-carbobenzoxy-3-(3,4-methylenedioxyphenyl)serine $[[\alpha]_D^{20} -27.9°$ (c=1.0, methanol)], were added 250 ml of dichloromethane and 14 ml of ethylmercaptan. To the mixture, while being cooled at 5° C. and stirred, was added 13.0 g of aluminum chloride. After 4 hours of reaction, the reaction mixture was treated and purified as in (1) above to yield 5.1 g of an amorphous powder of L-threo-N-carbobenzoxy-3-(3,4-dihydroxyphenyl)serine.

IR (Nujol) $\nu(cm^{-1})$: 3500–3250 (broad), 1740–1670 (broad), 1390, 1440, 1040, 930.

$[\alpha]_D^{20} -27.4°$ (c=1.0, methanol).

(2) To 1.0 g of D-threo-N-carbobenzoxy-3-(3,4-methylenedioxyphenyl)serine $[[\alpha]_D^{20} +28.0°$ (c=1.0, methanol)], were added 25 ml of methylene chloride and 3.4 g of n-octylmercaptan. To the mixture while being cooled at 5° C. and stirred, was added 1.5 g of aluminum chloride. After 6 hours of stirring, the reaction mixture was treated and purified as in (1) above to obtain 0.56 g of an amorphous powder of D-threo-N-carbobenzoxy-3-(3,4-dihydroxyphenyl)serine.

IR (Nujol) $\nu(cm^{-1})$: 3500–3250 (broad), 1740–1670 (broad), 1390, 1440, 1040, 930.

$[\alpha]_D^{20} = 27.3°$ (c=1.0, methanol).

(3) Using 8.0 g of L-threo-N-carbobenzoxy-3-(3,4-methylenedioxyphenyl)serine $[[\alpha]_D^{20} -27.9°$ (c=1.0, methanol)], 250 ml of dichloromethane, 36.8 g of n-dodecylmercaptan, and 12.3 g of aluminum chloride, the reaction, after-treatment and purification were carried out as in (1) above to obtain 6.2 g of an amorphous powder of L-threo-N-carbobenzoxy-3-(3,4-dihydroxyphenyl)serine.

$[\alpha]_D^{20} -27.5°$ (c=1.0, methanol).

(4) To a solution of 10.0 g of L-threo-N-carbobenzoxy-3-(3,4-methylenedioxyphenyl)serine $[[\alpha]_D^{20} -27.9°$ (c=1.0, methanol)] in 200 ml of methylene chloride, were added at room temperature 31 g of pyridine and 46 g of aluminum chloride. The mixture was stirred for 3 hours and, while being cooled in ice, mixed with 200 ml of 3-% hydrochloric acid. The mixture was allowed to separate into layers and the aqueous layer was extracted with ethyl acetate. The ethyl acetate layer was washed with water, dried over anhydrous magnesium sulfate, and stripped of the solvent by concentration under reduced pressure. The residue was purified by silica gel column chromatography (eluent: acetonitrile/benzene/acetic acid=4.5/4.5/1) to give 2.8 g of an amorphous powder of L-threo-N-carbobenzoxy-3-(3,4-dihydroxyphenyl)serine.

$[\alpha]_D^{20} -27.0°$ (c=1.0, methanol).

(5) To 1.0 g of L-threo-N-carbobenzoxy-3-(3,4-methylenedioxyphenyl)serine $[[\alpha]_D^{20} -26.8°$ (c=1.0, methanol)], were added 50 ml of dichloromethane and 2.7 ml of ethylmercaptan. To the mixture, while being cooled at 5° C. or below in iced water, was added 1.5 g of aluminum bromide. After 30 minutes of reaction, the reaction mixture was mixed with 50 ml of 3-% hydrochloric acid. The after-treatment and purification were carried out as in (4) above to yield 0.58 g of L- threo-N-carbobenzoxy-3-(3,4-dihydroxyphenyl)serine.

$[\alpha]_D^{20} -25.7°$ (c=1.0, methanol).

(6) To a solution of 1.0 g of L-threo-N-carbobenzoxy-3-(3,4-methylenedioxyphenyl)serine $[[\alpha]_D^{20} -26.8°$ (c=1.0, methanol)] in 50 ml of dichloromethane, while being cooled at 5° C. or below in iced water, was added 2.2 g of titanium tetrachloride. The mixture was allowed to react at room temperature for 1 hour. The reaction mixture was mixed with 50 ml of 3-% hydrochloric acid, while being cooled in iced water, and allowed to separate into layers. The aqueous layer was extracted with ethyl acetate and the extract was washed with water, dried, and stripped of the solvent by distillation. The residue was purified by silica gel chromatography to yield 0.22 g of L-threo-N-carbobenzoxy-3-(3,4-dihydroxyphenyl)serine in the form of amorphous powder.

$[\alpha]_D^{20} -26.3°$ (c=1.0, methanol).

EXAMPLE 9

Synthesis of optically active threo-N-carbobenzoxy-3-(3,4-dihydroxyphenyl)serine from racemate.

(1) Into a mixture of 400 ml of methanol and 250 ml of water, was dissolved at room temperature 50.0 g of racemic threo-N-carbobenzoxy-3-(3,4-dihydroxyphenyl)serine followed by the addition of 41.8 g of cinchonidine. After 20 minutes of stirring, the mixture was heated to 50° C. and allowed to cool gradually down to 20° C. over a period of 2 hours. The mixture was stirred at 15° to 20° C. for 3 hours. The precipitated crystals were collected by filtration to yield 40.2 g of L-threo-N-carbobenzoxy-3-(3,4-dihydroxyphenyl)serine cinchonidine salt; mp. 140° C. (decomp.);

$[\alpha]_D^{20} -64.0°$ (c=1.0, methanol).

A 22 g portion of the cinchonidine salt was decomposed by the addition of 80 ml of 3-% hydrochloric acid and extracted with 240 ml of ethyl acetate. The extract gave 11.3 g of amorphous powder of L-threo-N-carbobenzoxy-3-(3,4-dihydroxyphenyl)serine;

$[\alpha]_D^{20} -25.9°$ (c=1.0, methanol).

IR (Nujol) $\nu(cm^{-1})$: 3600–3100 (broad), 1660–1760 (broad), 1600, 1520, 1340, 1270, 1050.

The mother liquor from which the crystallized cinchonidine salt had been removed by filtration was stripped of the methanol by distillation under reduced pressure, admixed with 120 ml of 3-% hydrochloric acid, and extracted with ethyl acetate to yield 29.3 g of an amorphous powder of D-threo-N-carbobenzoxy-3-(3,4-dihydroxyphenyl)serine.

$[\alpha]_D^{20} +17.4°$ (c=1.0, methanol).

IR (Nujol) $\nu(cm^{-1})$; 3600–3100 (broad), 1760–1660 (broad), 1600, 1520, 1340, 1270, 1050.

To a solution of 8.9 g of the above D-threo-N-carbobenzoxy-3-(3,4-dihydroxyphenyl)serine in 260 ml of ethyl acetate, was added at room temperature 2.7 g of benzylamine. The precipitated crystals were collected by filtration to yield 10.9 g of D-threo-N-carbobenzoxy-3-(3,4-dihydroxyphenyl)serine benzylamine salt; mp. 145° C. (decomp.); $[\alpha]_D^{20} -5.3°$ (c=1.0, methanol).

(2) To a solution of 0.5 g of racemic threo-N-carbobenzoxy-3-(3,4-dihydroxyphenyl)serine in 5 ml of dioxane, was added 0.62 g of brucine. The mixture was stirred at room temperature for 15 hours. The precipitated crystals were collected by filtration to yield 0.21 g of D-threo-N-carbobenzoxy-3-(3,4-dihydroxyphenyl)serine brucine salt; mp. 139° C. (decomp.); $[\alpha]_D^{20} -1.9°$ (c=1.0, methanol).

A 0.2 g portion of the salt was decomposed with 3-% hydrochloric acid, and extracted with ethyl acetate to recover 0.08 g of an amorphous powder of D-threo-N-carbobenzoxy-3-(3,4-dihydroxyphenyl)serine;

$[\alpha]_D^{20} +25.5°$ (c=1.0, methanol).

(3) To a solution of 0.5 g of racemic threo-N-carbobenzoxy-3-(3,4-dihydroxyphenyl)serine in 5 ml of isopropyl alcohol, was added 0.33 g of S-2-amino-1,1-diphenylpropanol. The mixture was stirred at room temperature for 1 hour. The precipitated crystals were collected by filtration to yield 0.30 g of L-threo-N-carbobenzoxy-3-(3,4-dihydroxyphenyl)serine S-amino-1,1-diphenylpropanol salt; mp. 167° C. (decomp.); $[\alpha]_D^{20} +31.5°$ (c=1.0, methanol).

A 0.2 g portion of the salt was decomposed with 3-% hydrochloric acid and extracted with ethyl alcohol to yield 0.12 g of amorphous powder of L-threo-N-carbobenzoxy-3-(3,4-dihydroxyphenyl)serine;

$[\alpha]_D^{20} -26.3°$ (c=1.0, methanol).

(4) To a solution of 0.5 g of racemic threo-N-carbobenzoxy-3-(3,4-dihydroxyphenyl)serine in 10 ml of acetonitrile, was added 0.48 g of l-ephedrine. The mixture was left standing at room temperature for 10 days. The precipitated crystals were collected by filtration to yield 0.24 g of D-threo-N-carbobenzoxy-3-(3,4-dihydroxyphenyl)serine l-ephedrine salt; mp. 104° C. (decomp.); $[\alpha]_D^{20} - 21.5°$ (c=1.0, methanol).

A portion of the salt was decomposed with 3-% hydrochloric acid and extracted with ethyl acetate to yield 0.1 g of D-threo-N-carbobenzoxy-3-(3,4-dihydroxyphenyl)serine; $[\alpha]_D^{20} + 20.5°$ (c=1.0, methanol).

EXAMPLE 10

Preparation of optically active threo-3-(3,4-methylenedioxyphenyl)serine from optically active threo-N-carbobenzoxy-3-(3,4-methylenedioxyphenyl)serine.

To a solution of 12.7 g of L-threo-3-(3,4-methylenedioxyphenyl)-N-carbobenzoxyserine [$[\alpha]_D^{20} - 28.1°$ (c=1.0, methanol)] in 110 ml of methanol, were added 1.27 g of 10% Pd-C (50% wet) and 12.7 g of water. The mixture was subjected to hydrogenolysis at atmospheric pressure. After the hydrogen had been absorbed no more, 5.03 g of concentrated hydrochloric acid was added to the reaction mixture, stirred, and removed of the insolubles by filtration. The filtrate was adjusted to pH about 5.5 with a 30% aqueous sodium hydroxide solution. The precipitated crystals were collected by filtration and recrystallized from water to yield 5.20 g of L-threo-3-(3,4-methylenedioxyphenyl)serine: mp. 196°-198° C. (decomp.); $[\alpha]_D^{25} - 31.3°$ C. (c=1.0, N hydrochloric acid).

EXAMPLE 11

Preparation of optically active threo-3-(3,4-dihydroxyphenyl)serine from optically active threo-3-(3,4-methylenedioxyphenyl)serine.

To a solution of 4.50 g of the L-threo-3-(3,4-methylenedioxyphenyl)serine in 25 ml of 1,2-dichloroethane, while being cooled at −15° C., was added dropwise a solution of 12.5 g of boron trichloride in 1,2-dichloroethane. The mixture was stirred at −15° to −10° C. for 30 minutes, diluted with 40 ml of saturated aqueous sodium chloride solution, and further stirred at 0° to 5° C. for 20 minutes. The precipitate was collected by filtration, then dissolved in 50 ml of water, and, while being cooled at 0° to 5° C., adjusted to pH about 2 with a 30% aqueous sodium hydroxide solution, and 1.2 g of calcium hydroxide was dissolved in the mixture. The mixture was adjusted to pH about 9.5 with a 30% aqueous sodium hydroxide solution and left standing overnight at 0° to 4° C. The precipitated crystals were removed by filtration and the filtrate was adjusted to pH 4.7 with concentrated hydrochloric acid and left standing overnight at 0° to 3° C. The precipitated crystals were collected by filtration to yield 1.5 g of crude L-threo-3-(3,4-dihydroxyphenyl)serine which gave, upon recrystallization from water, 0.30 g L-threo-3-(3,4-dihydroxyphenyl)serine; mp. 228°-233° C.; $[\alpha]_D^{25} - 39.0$ (c=1.0, N hydrochloric acid).

EXAMPLE 12

Preparation of racemic threo-3-(3,4-dihydroxyphenyl)serine from racemic threo-N-carbobenzoxy-3-(3,4-dihydroxyphenyl)serine.

To a mixture of 11.8 g of racemic threo-N-carbobenzoxy-3-(3,4-dihydroxyphenyl)serine [mp. 145°-146° C. (decomp.)], 120 ml of methanol, and 12.0 ml of water, was added 1.2 g of 5-% palladium-carbon (50% wet). The mixture was subjected to catalytic reduction under a hydrogen stream. After completion of the reaction, the reaction mixture was mixed with 4.0 g of concentrated hydrochloric acid and stirred for 20 minutes. The insolubles were removed by filtration and washed with methanol. The filtrate and the washings were combined, adjusted to pH 5.5-6.0 with a 30% aqueous sodium hydroxide solution, and stirred at 0° to 5° C. for 2 hours. The precipitated crystals were collected by filtration to give 6.8 g of racemic threo-3-(3,4-dihydroxyphenyl)serine [mp. 211°-220° C. (decomp.)].

EXAMPLE 13

Synthesis of optically active threo-3-(3,4-dihydroxyphenyl)serine.

(1) To a mixture of 2.36 g of L-threo-N-carbobenzoxy-3-(3,4-dihydroxyphenyl)serine [$[\alpha]_D^{20} - 27.4°$ (c=1.0, methanol)], 24 ml of methanol, and 2.4 ml of water, was added 0.24 g of 5% palladium-carbon (50% wet). The mixture was subjected to catalytic reduction under a hydrogen stream. After completion of the reaction, the reaction mixture was mixed with 0.8 g of concentrated hydrochloric acid and stirred for 20 minutes. The insolubles were separated by filtration and washed with methanol. The filtrate and the washings were combined and adjusted to pH 5.5-6.0 with a 30-% aqueous sodium hydroxide solution to precipitate crystals. The mixture was stirred at 0° to 5° C. for 2 hours. The precipitated crystals were collected by filtration to give 1.33 g (91.9% yield) of L-threo-3-(3,4-dihydroxyphenyl)serine; $[\alpha]_D^{20} - 39.7°$ (c=1.0, 1N hydrochloric acid); mp. 215° C. (decomp.).

A 1.2 g portion of the L-threo-3-(3,4-dihydroxyphenyl)serine was recrystallized from 76 ml of water containing 0.01 g of L-ascorbic acid to give 0.96 g (80.0% yield) of purified L-threo-3-(3,4-dihydroxyphenyl)serine [$[\alpha]_D^{20} - 40.7°$ (c=1.0, N hydrochloric acid); mp. 226° C. (decomp.)].

(2) To a mixture of 3.0 g of L-threo-N-carbobenzoxy-3-(3,4-dihydroxyphenyl)serine [$[\alpha]_D^{20} - 27.5°$ (c=1.0, methanol)], 15 ml of methanol, 15 ml of ethyl acetate, and 3 ml of water, was added 0.3 g of 5% palladium-carbon (50% wet). The mixture was subjected to catalytic reduction under a hydrogen stream. After completion of the reaction, the reaction mixture was mixed with 1.0 g of concentrated hydrochloric acid and stirred for 20 minutes. The insolubles were separated and washed with methanol. The filtrate and the washings were combined and adjusted to pH 5.5-6.0 with a 30% aqueous sodium hydroxide solution to precipitate crystals. After two hours of stirring at 0° to 5° C., the precipitated crystals were collected by filtration to give 1.67 g (90.5% yield) of L-threo-3-(3,4-dihydroxyphenyl)serine [$[\alpha]_D^{20} - 37.3°$ (c=1.0, N hydrochloric acid); mp. 214° C. (decomp.)].

A 1.5 g portion of this compound was recrystallized from 96 ml of water containing 0.02 g of L-ascorbic acid to give 1.2 g (80.5% yield) of purified L-threo-3-(3,4-dihydroxyphenyl)serine; $[\alpha]_D^{20} - 40.4°$ (c=1.0, N hydrochloric acid); mp. 226° C. (decomp.).

What is claimed is:

1. A process for producing threo-3-(3,4-dihydroxyphenyl)serine represented by the formula

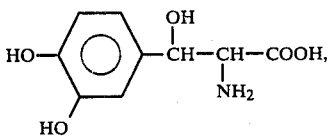

which comprises treating threo-3-(3,4-methylenedioxyphenyl)serine or an N-carbobenzoxy derivative thereof represented by the formula

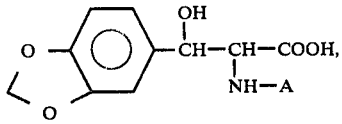

wherein A represents a hydrogen atom or a carbobenzoxy group, with a Lewis acid to form threo-3-(3,4-dihydroxyphenyl)serine or an N-carbobenzoxy derivative thereof represented by the formula

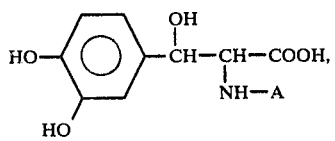

wherein A is as defined above, and, if A is a carbobenzoxy group, catalytically reducing the resulting compound of formula [2].

2. A process according to claim 1, wherein each of the compounds represented by the formula [1], [2] or [3] is an optically active compound.

3. A process according to claim 1, wherein A of the formulas [2] and [3] is a hydrogen atom.

4. A process according to claim 1, wherein A of the formulas [2] and [3] is a carbobenzoxy group.

5. A process according to claim 4, wherein each of the compounds represented by the formula [1], [2] or [3] is an optically active compound.

6. A process for producing an optically active threo-3-(3,4-dihydroxyphenyl)serine represented by the formula

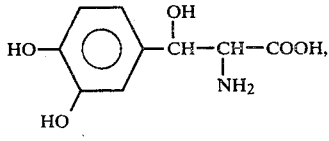

which comprises reacting racemic threo-N-carbobenzoxy-3-(3,4-methylenedioxyphenyl)serine with one optically active amine selected from the group consisting of ephedrine, quinidine, quinine and 2-amino-1,1-diphenylpropanol to form a mixture of amine salts of D- and L-threo-N-carbobenzoxy-3-(3,4-methylenedioxyphenyl)serine, separating the mixture by taking advantage of the solubility difference into the amine salt of D-threo-N-carbobenzoxy-3-(3,4-methylenedioxyphenyl)serine and the amine salt of L-threo-N-carbobenzoxy-3-(3,4-methylenedioxyphenyl)serine, reacting each amine salt with an acid to obtain an optically active (D- or L-) threo-N-carbobenzoxy-3-(3,4-methyleneoxyphenyl)serine, reacting the resulting optically active compound with a Lewis acid to yield an optically active threo-N-carbobenzoxy-3-(3,4-dihydroxyphenyl)serine, and catalytically reducing the resulting compound.

7. A process for producing an optically active threo-3-(3,4-dihydroxyphenyl)serine represented by the formula

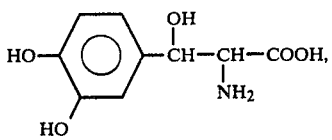

which comprises treating racemic threo-N-carbobenzoxy-3-(3,4-methylenedioxyphenyl)serine with a Lewis acid to yield racemic threo-N-carbobenzoxy-3-(3,4-dihyroxyphenyl)serine, reacting the resulting compound with one optically active amine selected from the group consisting of cinchonidine, brucine, ephedrine, and 2-amino-1,1-diphenylpropanol to convert the racemic mixture into a mixture of amine salts of D- and L-threo-N-carbobenzoxy-3-(3,4-dihydroxyphenyl)serine, separating the mixture by taking advantage of the solubility difference into the amine salt of D-threo-N-carbobenzoxy-3-(3,4-dihydroxyphenyl)serine and the amine salt of L-threo-N-carbobenzoxy-3-(3,4-dihydroxyphenyl)serine, reacting each amine salt with an acid to obtain an optically active threo-N-carbobenzoxy-3-(3,4-dihydroxyphenyl)serine, and catalytically reducing the resulting optically active compound.

8. A process for producing an optically active threo-3-(3,4-dihyroxyphenyl)serine represented by the formula

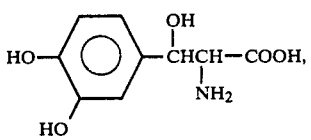

which comprises reacting glycine with piperonal in the presence of a base, adding acetic acid to the reaction mixture to obtain acetate of the racemic threo-3-(3,4-methylenedioxyphenyl)serine represented by the formula

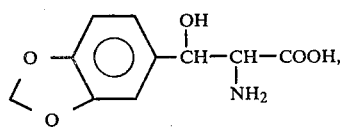

reacting said acetate with carbobenzoxy chloride to yield racemic threo-N-carbobenzoxy-3-(3,4-methylenedioxyphenyl)serine represented by the formula

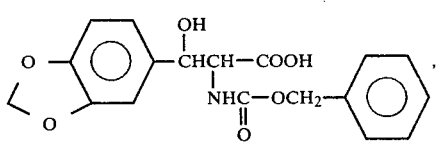

subjecting the resulting racemic mixture to optical resolution by use of an optically active amine selected from the group consisting of ephedrine, quinidine, quinine, and 2-amino-1,1-diphenylpropanol to yield an optically active threo-N-carbobenzoxy-3-(3,4-methylenedioxyphenyl)serine, treating the resulting optically active compound with a Lewis acid to convert the former to optically active threo-N-carbobenzoxy-3-(3,4-dihydroxyphenyl)serine represented by the formula

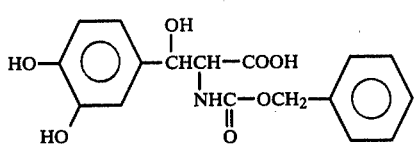

[2']

and catalytically reducing the resulting optically active compound.

9. A process for producing an optically active threo-3-(3,4-dihydroxyphenyl)serine represented by the formula

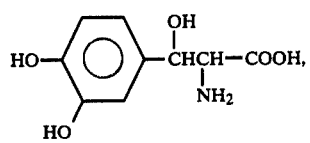

[1]

which comprises reacting glycine with piperonal in the presence of a base, adding acetic acid to the reaction mixture to obtain acetate of the racemic threo-3-(3,4-methylenedioxyphenyl)serine represented by the formula

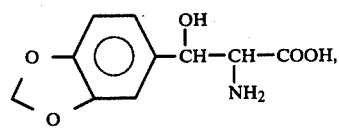

[3']

reacting said acetate with carbobenzoxy chloride to yield racemic threo-N-carbobenzoxy-3-(3,4-methylenedioxyphenyl)serine represented by the formula

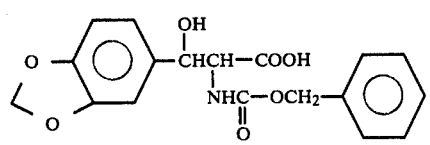

[3"]

treating the resulting compound with a Lewis acid to yield racemic threo-N-carbobenzoxy-3-(3,4-dihydroxyphenyl)serine, subjecting the resulting racemic mixture to optical resolution by use of an optically active amine selected from the group consisting of cinchonidine, brucine, ephedrine, and 2-amino-1,1-diphenylpropanol to obtain an optically active threo-N-carbobenzoxy-3-(3,4-dihydroxyphenyl)serine, and catalytically reducing the resulting optically active compound.

10. A process for producing racemic or optically active threo-3-(3,4-dihydroxyphenyl)serine represented by the formula

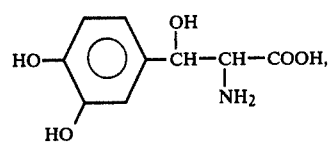

[1]

which comprises reacting glycine with piperonal in the presence of a base, adding acetic acid to the reaction mixture to obtain acetate of the racemic threo-3-(3,4-methylenedioxyphenyl)serine represented by the formula

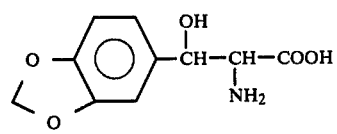

[3']

and treating said acetate, either as such or after having been resolved into optically active isomers, with a Lewis acid.

11. Threo-N-Carbobenzoxy-3-(3,4-methylenedioxyphenyl)serine represented by the formula

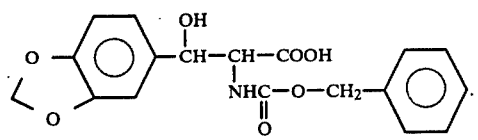

[3"]

12. An optically active threo-N-carbobenzoxy-3-(3,4-methylenedioxyphenyl)serine represented by the formula

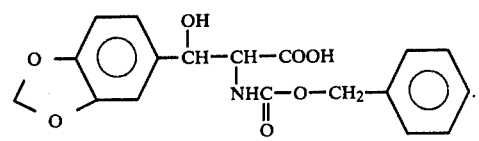

[3"]

13. A process for producing a threo-N-carbobenzoxy-3-(3,4-methylenedioxyphenyl)serine represented by the formula

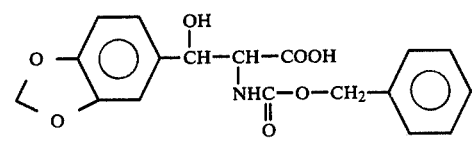

[3"]

which comprises reacting glycine with piperonal in the presence of a base, adding acetic acid to the reaction mixture to obtain acetate of racemic threo-3-(3,4-methylenedioxyphenyl)serine, reacting said acetate with carbobenzoxy chloride, and, if necessary, subjecting the resulting racemic threo-N-carbobenzoxy-3-(3,4-methylenedioxyphenyl)serine to optical resolution through the salt formation with an optically active amine.

* * * * *